(12) United States Patent
Steel

(10) Patent No.: US 10,669,575 B2
(45) Date of Patent: Jun. 2, 2020

(54) SQUARE WAVE THERMAL CYCLING

(71) Applicant: Becton, Dickinson and Company, Franklin Lakes, NJ (US)

(72) Inventor: Adam Steel, Fallston, MD (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 219 days.

(21) Appl. No.: 15/687,232

(22) Filed: Aug. 25, 2017

(65) Prior Publication Data

US 2018/0163252 A1    Jun. 14, 2018

Related U.S. Application Data

(60) Division of application No. 14/249,647, filed on Apr. 10, 2014, now Pat. No. 9,745,623, which is a continuation of application No. PCT/US2012/059816, filed on Oct. 11, 2012.

(60) Provisional application No. 61/547,199, filed on Oct. 14, 2011.

(51) Int. Cl.
| C12Q 1/68 | (2018.01) |
| C12Q 1/686 | (2018.01) |
| B01L 7/00 | (2006.01) |
| C12Q 1/6813 | (2018.01) |

(52) U.S. Cl.
CPC ............. *C12Q 1/686* (2013.01); *B01L 7/52* (2013.01); *C12Q 1/6813* (2013.01); *C12Q 2527/107* (2013.01); *C12Q 2527/15* (2013.01)

(58) Field of Classification Search
CPC ................................ C12Q 1/68; C07H 21/00
See application file for complete search history.

(56) References Cited

U.S. PATENT DOCUMENTS

| 4,469,863 | A | 9/1984 | Ts'o |
| 5,034,506 | A | 7/1991 | Summerton et al. |
| 5,216,141 | A | 6/1993 | Benner |
| 5,235,033 | A | 8/1993 | Summerton et al. |
| 5,386,023 | A | 1/1995 | Sanghvi et al. |
| 5,602,240 | A | 2/1997 | De Mesmaeker et al. |
| 5,637,684 | A | 6/1997 | Cook et al. |
| 5,644,048 | A | 7/1997 | Yau |
| 5,705,333 | A | 1/1998 | Shah et al. |
| 6,140,054 | A | 10/2000 | Wittwer et al. |
| 6,346,386 | B1 | 2/2002 | Elenitoba-Johnson |
| 6,664,064 | B1 | 12/2003 | Dietmaier |
| 7,273,699 | B2* | 9/2007 | Lipsky .................. C12Q 1/6827 435/6.1 |
| 7,273,700 | B2 | 9/2007 | Kurane et al. |
| 7,297,484 | B2 | 11/2007 | Wittwer et al. |
| 7,670,832 | B2 | 3/2010 | Wittwer et al. |
| 8,455,190 | B2 | 6/2013 | Makrigiorgos |
| 8,691,504 | B2 | 4/2014 | Li et al. |
| 9,745,623 | B2 | 8/2017 | Steel |
| 2002/0058258 | A1 | 5/2002 | Wittwer et al. |
| 2004/0222384 | A1* | 11/2004 | Lee ................ B01L 7/52 250/458.1 |
| 2005/0051974 | A1* | 3/2005 | Dobson .............. B60G 7/005 277/635 |
| 2006/0094108 | A1* | 5/2006 | Yoder .................. B01L 3/508 435/287.2 |
| 2007/0026421 | A1* | 2/2007 | Sundberg ........... B01L 3/5027 435/6.12 |
| 2007/0212704 | A1 | 9/2007 | Dong et al. |
| 2007/0224598 | A1 | 9/2007 | Chang |
| 2008/0269065 | A1 | 10/2008 | Lyon et al. |
| 2009/0297475 | A1* | 12/2009 | Waring ............. A61K 38/2026 424/85.5 |
| 2010/0203532 | A1* | 8/2010 | Makrigiorgos ...... C12Q 1/6858 435/6.12 |
| 2010/0248237 | A1 | 9/2010 | Froehlich et al. |
| 2011/0039720 | A1 | 2/2011 | Vossenaar et al. |
| 2014/0017670 | A1 | 1/2014 | Yu et al. |
| 2014/0227702 | A1 | 8/2014 | Guo et al. |
| 2014/0272927 | A1 | 9/2014 | Coursey et al. |
| 2015/0376692 | A1 | 12/2015 | Esfandyarpour et al. |

FOREIGN PATENT DOCUMENTS

| CN | 1153536 A | 7/1997 |
| CN | 1934270 A | 3/2007 |
| CN | 101198706 A | 6/2008 |
| CN | 101663408 A | 3/2010 |
| JP | 2002525128 A | 8/2002 |
| JP | 2009-509565 | 3/2009 |
| JP | 2009-525759 | 7/2009 |
| JP | 2010-193884 | 9/2010 |

OTHER PUBLICATIONS

Allawi et al., Thermodynamics of internal C-T mismatches in DNA. Nucl Acids Res. (1998) 26(11):2694-2701.

Amosova O. et al., Effect of the 1-(2'_deoxy-beta-D-ribofuranosyl)-3-nitropyrrole Residue on the Stability of DNA Duplexes and Triplexes. Nucl Acids Res. (1997) 25(10):1930-1934.

Beaucage S.L. et al., The Functionalization of Oligonucleotides Via Phosphoramidite Derivatives. Tetrahedon Report No. 329; Tetrahedron (1993) 49(10):1925-1963.

Bergstrom D.E. et al., Synthesis, Structure, and Deoxyribonucleic Acid Sequencing with a Universal Nucleoside: 1-(2'-Deoxy-beta-D-ribofuranosyl)-3-nitropyrrole. J Am Chem Soc. (1995) 117:1201-1209.

Bergstrom D.E. et al., Comparison of the Base Pairing Properties of a Series of Nitroazole Nucleobase Analogs in the Oligodeoxyribonucleotide Sequence 5'-d(CGCXAATTYGCG)-3'. Nucl Acids Res. (1997) 25(10):1935-1942.

Brill W. K.-D. et al., Synthesis of Oligodeoxynucleoside Phosphorodithiotes via Thioamidites. J Am Chem Soc. (1989) 111:2321-2322.

Carlsson C. et al., Screening for Genetic Mutations. Nature (1996) 380:207.

(Continued)

*Primary Examiner* — Ethan C Whisenant

(74) *Attorney, Agent, or Firm* — Knobbe, Martens, Olson & Bear, LLP

(57) ABSTRACT

Embodiments disclosed herein relate to methods and systems for analysis of melting temperatures, and particularly to analysis of duplex nucleic acids.

17 Claims, 3 Drawing Sheets

(56) References Cited

OTHER PUBLICATIONS

De Mesmaeker A. et al., Comparison of Rigid and Flexible Backbones in Antisense Oligonucleotides. Biorg Med Chem Lttrs. (1994) 4(3):395-398.
Dempcy R.O. et al., Synthesis of a Thymidyl Pentamer of Deoxyribonucleic Guanidine and Binding Studies with DNA Homopolynucleotides. P.N.A.S. (1995) 92:6097-6101.
Egholm M. et al., Peptide Nucleic Acids (PNA). Oligonucleotide Analogues with an Achiral Peptide Backbone. J Am Chem Soc. (1992) 114:1895-1897.
Egholm M. et al., PNA Hybridizes to Complementary Oligonucleotides Obeying the Watson-Crick Hydrogen-Bonding Rules. Nature (1993) 365:566-568.
Gao et al., Unusual Conformation of a 3'-thioformacetal Linkage in a DNA Duplex. J Biomol. (1994) 4:17-34.
Horn et al., Oligonucleotides with Alternating Anionic and Cationic Phosphoramidate Linkages: Synthesis and Hybridization of Stereouniform Isomers. Tetrahed Ltts. (1996) 37(6):743-746.
Kubista et al., Review: The real-time polymerase chain reaction. Mol Aspects Med. (2006) 27:95-125.
Jenkins G.N. et al., The Biosynthesis of Carbocyclic Nucleosides. Chem Soc Rev. (1995) pp. 169-176.
Jing et al., "Effect of Salt Concentration on Melting Temperature of DNA Duplex Immobilized on Gold Nanoparticles"; J Yunnan Nationalities University (Natural Sciences Edition-China) (Jul. 2008) 17(3):193-196.
Jung P.M. et al., Hybridization of Alternating Cationic/Anionic Oligonucleotides to RNA Segments. Nucl Nucleo. (1994) 13(6 &7):1597-1605.
Letsinger R.L. et al., Phosphoramidate Analogs of Oligonucleotides. J Org Chem (1970) 35(11):3800-3803.
Letsinger R.L. et al., Effects of pendant groups of phosphorus on binding properties of d-ApA analogues. Nucl Acids Res. (1986) 14(8):3487-3499.
Letsinger R.L. et al., Cationic Oligonucleotides. J Am Chem Soc. (1988) 110:4470-4471.
Loakes D. et al., 5-Nitroindole as an Universal Base Analogue. Nucl Acids Res. (1994) 22(20):4039-4043.
Loakes D. et al., 3-Nitropyrrole and 5-Nitroindole as Universal Bases in Primers for DNA Sequencing and PCR. Nucl Acids Res. (1995) 23(13):2361-2366.
Ma H. et al., DNA Folding and Melting Observed in Real Time redefine the Energy Landscape. P.N.A.S. (2007) 104(3):712-716.
Mag et al. Synthesis and Selective Cleavage of an Oligodeoxynucleotide Containing a Bridged Internucleotide 5'-phosphorothioate Linkage. Nucl Acids Rex. (1991) 19(7):1437-1441.
Martin F.H. et al., Base Pairing Involving Deoxyinosine: Implications for Probe Design. Nucl Acids Res. (1985) 13(24):8927-8938.
Matray T.J. et al., A Specific Partner for Abasic Damage in DNA. Nature (1999) 399(6737:704-708.
Meier C. et al., Peptide Nucleic Acids (PNAs)—Unusual Properties of Nonionic Oligonucleotide Analogues. Angew Chem Int Ed Engl. (1992) 31(8):1008-1010.
Millican T.A. et al., Synthesis and Biophysical Studies of Short Oligodeoxynucleotides with Novel Modifications: A Possible Approach to the Problem of Mixed Base Oligodeoxynucleotide Synthesis. Nucl Acids Res. (1984) 12(19):7435-7453.

Mukumoto K. et al., Synthesis of Ferrocenylcarbodiimide as a Convenient Electrochemically Active Labeling Reagent for Nucleic Acids. Tetrahedron (2005) 61(49):11705-11715.
Nichols R. et al., a Universal Nucleoside for Use at Ambiguous Sites in DNA Primers. Nature (1994) 369:492-493.
Ogawa A.K. et al., Efforts toward the Expansion of the Genetic Alphabet: Information Storage and Replication with Unnatural Hydrophobic Base Pairs. J Am Chem Soc. (2000) 122:3274-3287.
Pals et al., A Rapid and Sensitive Approach to Mutation Detection Using Real-time Polymerase Chain Reaction and Melting Curve Analyses, Using BRCA1 as an Example. Mol Diagn. (1999) 4(3):241-246.
Pauwels et al., Biological Activity of New 2-5A Analogues. Chemica Scripta (1986) 26:141-145.
Rawls R.L. Optimistic about Antisense—Promising clinical results and chemical strategies for further improvements delight antisense drug researchers. Science/Tech.; C&E News, Jun. 2, 1997; pp. 35-39.
Ririe et al., Product differentiation by analysis of DNA melting curve during the polymerase chain reaction. Anal Biochem. (1997) 245(2): 154-160.
Rollo et al., A simple and low cost DNA amplifier. Nucl Acids Res. (1988) 16(7):3105-3106.
Sanghvi Y.S. et al. [Eds.], Carbohydrate Modifications in Antisense Research. ACS Symposium Series 580. American Chemical Society, Washington, DC. (1994)—TOC only.
Sawai, Hiroaki, Synthesis and Properties of Oligoadenylic Acids Containing 2'-5' Phosporamide Linkage. Chem Lttrs. The Chemical Society of Japan (1984) 805-808.
Schweitzer B.A. et al., Hydrophobic, Non-Hydrogen-Bonding Bases and Base Pairs in DNA. J Am Chem Soc. (1995) 117(7):1863-1872.
Sprinzl M. et al., Enzymatic Incorporation of ATP and CTP Analogues into the 3' End of tRNA. Eur J Biochem. (1977) 81:579-589.
Van Aerschot A. et al., An Acyclic 5-nitroindazole Nucleoside Analogue as Ambiguous Nucleoside. Nucl Acids Res. (1995) 23(21):4363-4370.
Von Kiedrowski G. et al., Parabolic Growth of a Self-Replicating Hexadeoxynucleotide Bearing a 3'-5'-Phosphoamidate Linkage. Angew Chem Int Ed Engl. (1991) 4:423-426.
Williams A.P. et al., Laser Temperature-Jump, Spectroscopic, and Thermodynaic Study of Salt Effects on Duplex Formation by dGCATGC. Biochemistry (1989) 28(10):4283-4291.
Wittwer et al., Continuous Fluorescence Monitoring of Rapid Cycle DNA Amplification. BioTechniques (1997) 22:130-138.
Wittwer et al., The LightCycler™: A Microvolume Multisample Fluorimeter with Rapid Temperature Control. (1997) 22:176-181.
Wittwer et al., Real-Time Multiplex PCR Assays. Methods (2001) 25:430-442.
Wittwer et al., High-Resolution Genotyping by Amplicon Melting Analysis Using LCGreen. Clin Chem. (2003) 49(6):853-860.
Zabost et al., Substantial difference between temperature dependencies of dsDNA predenaturation process . . . Phys Chem Chem Phys. (2009) 11:8933-8938.
Zhang P. et al., Exploratory Studies on Azole Carboxamides as Nucleobase Analogs: Thermal Denaturation Studies . . . Nucl Acids Res. (1998) 26(9):2208-2215.
International Search Report and Written Opinion dated Mar. 13, 2013 for Application No. PCT/US2012/059816, filed Oct. 11, 2012.
International Preliminary Report on Patentability dated Apr. 15, 2014 for Application No. PCT/US2012/059816, filed Oct. 11, 2012.

* cited by examiner

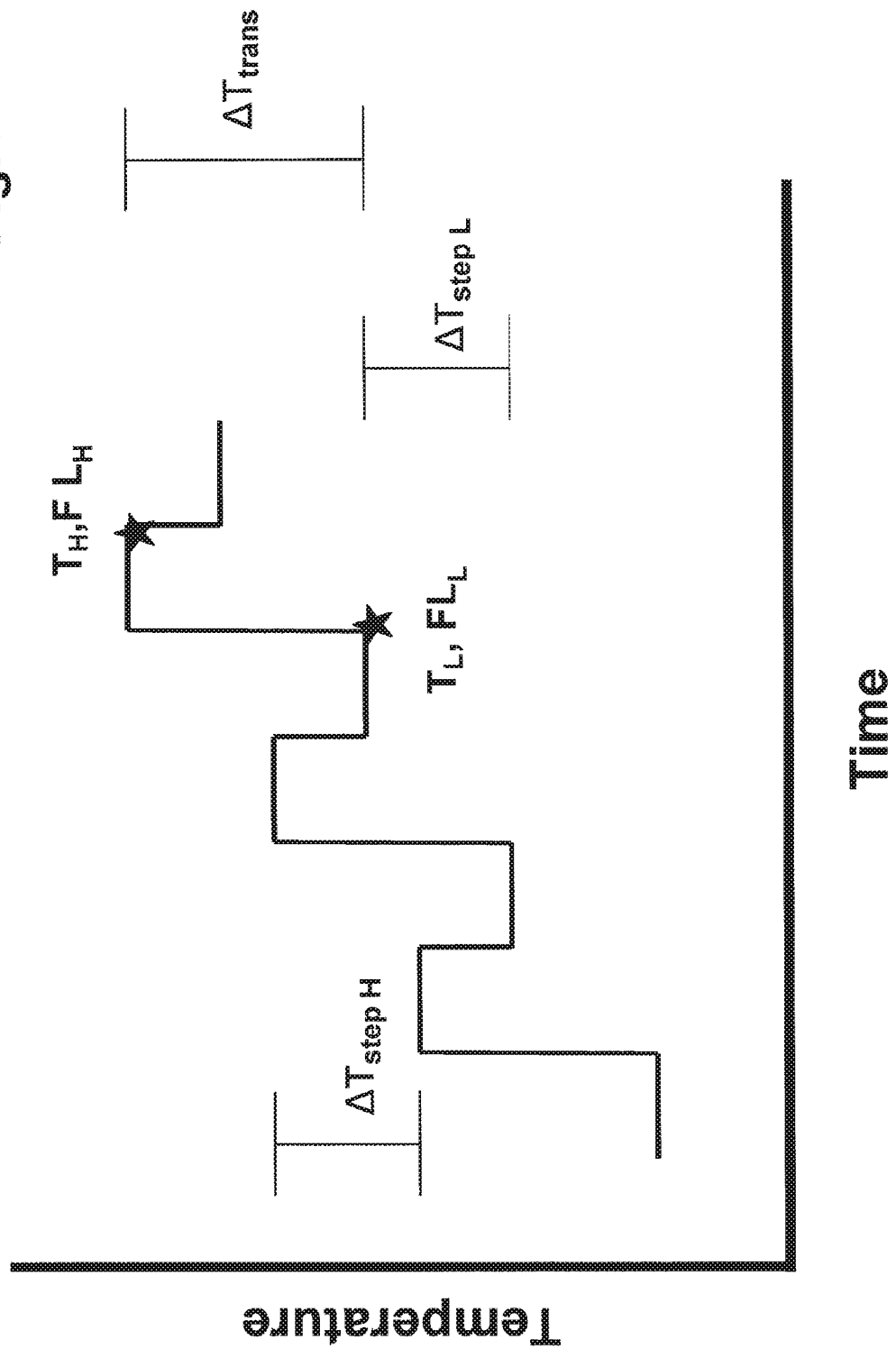

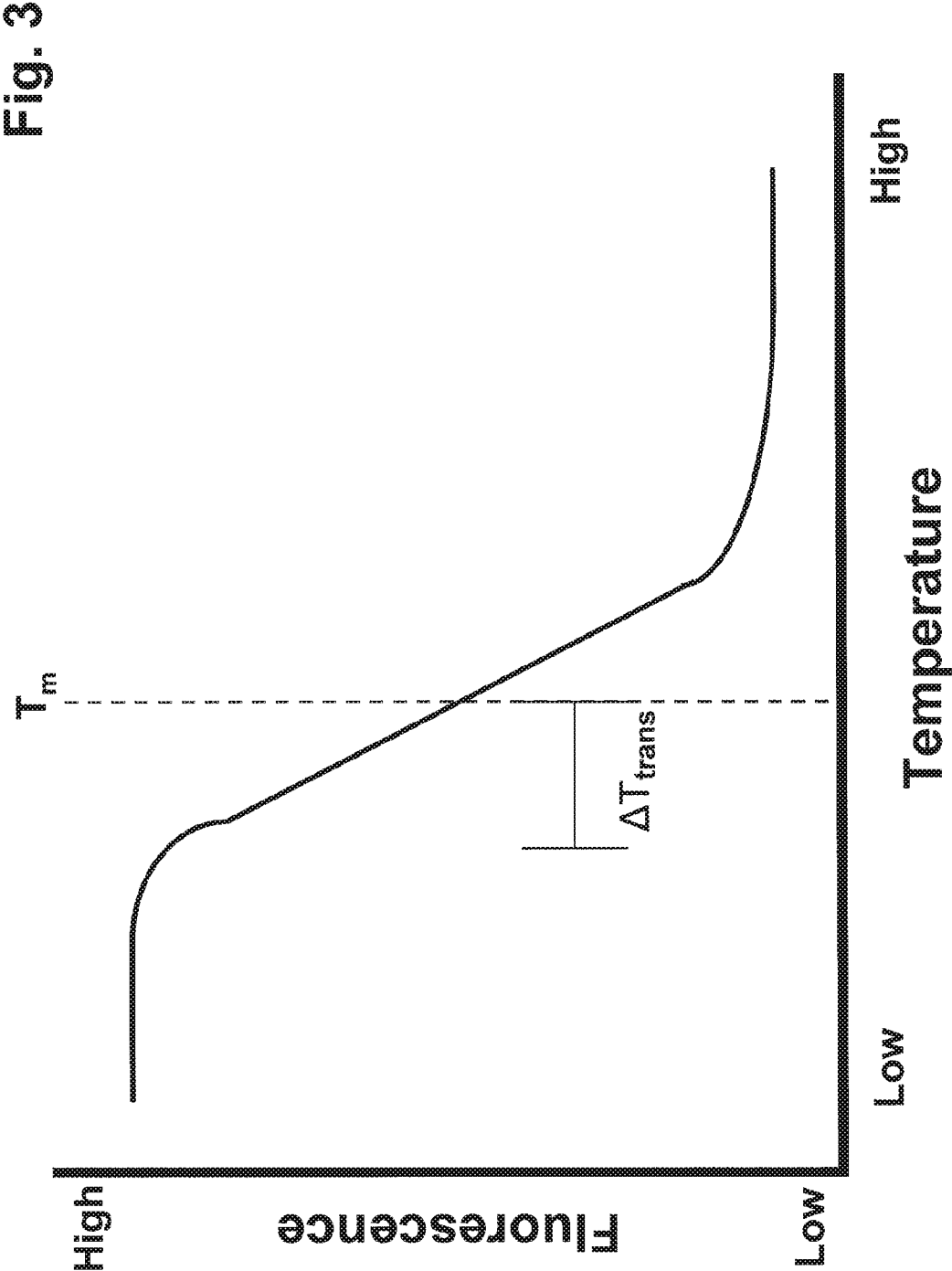

SQUARE WAVE THERMAL CYCLING

CROSS-REFERENCE TO RELATED APPLICATIONS

This application is a divisional of U.S. application Ser. No. 14/249,647, filed Apr. 10, 2014, and scheduled to issue as U.S. Pat. No. 9,745,623, on Aug. 29, 2017, which is a continuation of International Application Serial No. PCT/US2012/059816, filed Oct. 11, 2012, which claims priority to U.S. Provisional Application Ser. No. 61/547,199, filed on Oct. 14, 2011. Each of the above applications is hereby expressly incorporated by reference in its entirety.

BACKGROUND OF THE INVENTION

Field of the Invention

Embodiments disclosed herein relate to methods and systems for analysis of melting temperatures, and particularly to analysis of duplex nucleic acids.

Description of the Related Art

Melting curve analysis can be used to infer information about length, sequence, GC content and complementarity of duplex nucleic acids. As such, melting curve analysis is widely used in variety of applications, such as detecting single-nucleotide polymorphisms (SNP) and distinguishing between homozygous wild type, heterozygous and homozygous mutant alleles by virtue of the dissociation patterns produced. Additionally, melting curve analysis can be used to detect spurious amplification products after polymerase chain reaction (PCR).

However, currently-available melting curve analysis techniques have limitations, especially with respect to maintaining uniformity between samples and between repeated analyses. Thus, there is a need for methods and systems which improve the speed and accuracy of melting curve analysis of nucleic acids.

SUMMARY OF THE INVENTION

The present technology relates to methods and systems for analysis of nucleic acid melting curves, especially with regard to duplex nucleic acid molecules. In some embodiments of the present technology, such methods and systems permit the analysis of melting temperatures with improved speed and accuracy.

In some embodiments of the technology presented herein, methods of determining the melting temperature of a duplex nucleic acid molecule are provided that allow for improved speed and accuracy of nucleic acid melting curve analysis. The methods can include subjecting a solution comprising a double-stranded nucleic acid molecule to a square wave temperature gradient, the gradient comprising a range of temperatures that causes at least one transition of the double-stranded nucleic acid molecule to single-stranded nucleic acid molecules; and detecting the at least one transition over the course of the square wave temperature gradient.

In some embodiments, the square wave temperature gradient can comprise a series of temperature pulses, each pulse comprising: increasing the temperature of the solution to a first high temperature; decreasing the temperature of the solution to a second low temperature; wherein the first high temperature is greater than the second low temperature; and wherein, in subsequent pulses, the first high temperature and the second low temperature are each adjusted to be greater than the first and second temperatures, respectively, in prior pulses.

Also presented herein is a method of determining the melting temperature of a duplex nucleic acid molecule, the method comprising subjecting a solution comprising a plurality of single-stranded nucleic acid molecules to a square wave temperature gradient, the gradient comprising a range of temperatures that causes at least one transition of the single-stranded nucleic acid molecules to double-stranded nucleic acid molecules; and detecting the at least one transition over the course of the square wave temperature gradient.

In some embodiments, the square wave temperature gradient can comprise a series of temperature pulses, each pulse comprising: increasing the temperature of the solution to a first high temperature; decreasing the temperature of the solution to a second low temperature; wherein the first high temperature is greater than the second low temperature; and wherein, in subsequent pulses, the first high temperature and the second low temperature are each adjusted to be less than the first and second temperatures, respectively, in prior pulses.

Also presented herein is a system for determining the melting temperature of a duplex nucleic acid molecule, the system comprising a programmable thermal cycling apparatus; a detector; and a program for square wave thermal cycling, the program comprising instructions for: subjecting a solution comprising a double-stranded nucleic acid molecule to a square wave temperature gradient, the gradient comprising a range of temperatures that causes at least one transition of the double-stranded nucleic acid molecule to a single-stranded nucleic acid molecules; and detecting the at least one transition over the course of the square wave temperature gradient.

In some embodiments of the above system, the square wave temperature gradient comprises a series of temperature pulses, each pulse comprising: increasing the temperature of the solution to a first high temperature; decreasing the temperature of the solution to a second low temperature; wherein the first high temperature is greater than the second low temperature; and wherein, in subsequent pulses, the first high temperature and the second low temperature are each adjusted to be greater than the first and second temperatures, respectively, in prior pulses.

Also presented herein is a method of determining melting temperature of a double-stranded nucleic acid molecule, the method comprising: providing a sample comprising double-stranded nucleic acid molecules and a reporter moiety having a signature detectable signal in the presence of duplex nucleic acid; subjecting the sample to a series of temperature pulses, wherein at least a plurality of the pulses cause the double-stranded nucleic acid molecules to transition to single-stranded molecules and back to double-stranded molecules; and detecting, using the signal produced by the reporter moiety, the melting temperature of the double-stranded nucleic acid molecule.

In some embodiments, each of the temperature pulses comprises: increasing the temperature of the solution to a first high temperature; decreasing the temperature of the solution to a second low temperature; wherein the first high temperature is greater than the second low temperature; and wherein, in subsequent pulses, the first high temperature and the second low temperature are each adjusted to be greater than the first and second temperatures, respectively, in prior pulses.

Also provided herein is a method of determining kinetic information about a double-stranded to single-stranded transition for nucleic acids, the method comprising: providing a sample comprising double-stranded nucleic acid molecules and a reporter moiety having a signature detectable signal in the presence of duplex nucleic acid; subjecting the sample to a series of temperature pulses, wherein the pulses cause the double-stranded nucleic acid molecules to transition to single-stranded molecules and back to double-stranded molecules; and detecting, using the signal produced by the reporter moiety, the rate of transition between single-stranded and double-stranded states, whereby the rate of transition between the states provides kinetic information about the transition.

Also presented herein is a method of determining the melting temperature of a duplex nucleic acid molecule, the method comprising: subjecting a solution comprising single-stranded nucleic acid molecules to a square wave temperature gradient, the gradient comprising a range of temperatures that causes at least one transition of the single-stranded nucleic acid molecules to double-stranded nucleic acid molecules; and detecting the at least one transition over the course of the square wave temperature gradient.

In some embodiments, the square wave temperature gradient can comprise a series of temperature pulses, each pulse comprising: increasing the temperature of the solution to a first high temperature; decreasing the temperature of the solution to a second low temperature; wherein the first high temperature is greater than the second low temperature; and wherein, in subsequent pulses, the first high temperature and the second low temperature are each adjusted to be less than the first and second temperatures, respectively, in prior pulses.

BRIEF DESCRIPTION OF THE DRAWINGS

FIG. 2 is a graph showing one example of a square wave temperature profile, with temperature shown in the Y-axis and time shown in the X-axis.

FIG. 3 is a graph showing traditional melting curve analysis. A fluorescent signal, indicative of double-stranded nucleic acid, is shown in the Y-axis. Temperature is shown in the X-axis.

DETAILED DESCRIPTION OF THE PREFERRED EMBODIMENT

Figure 1:
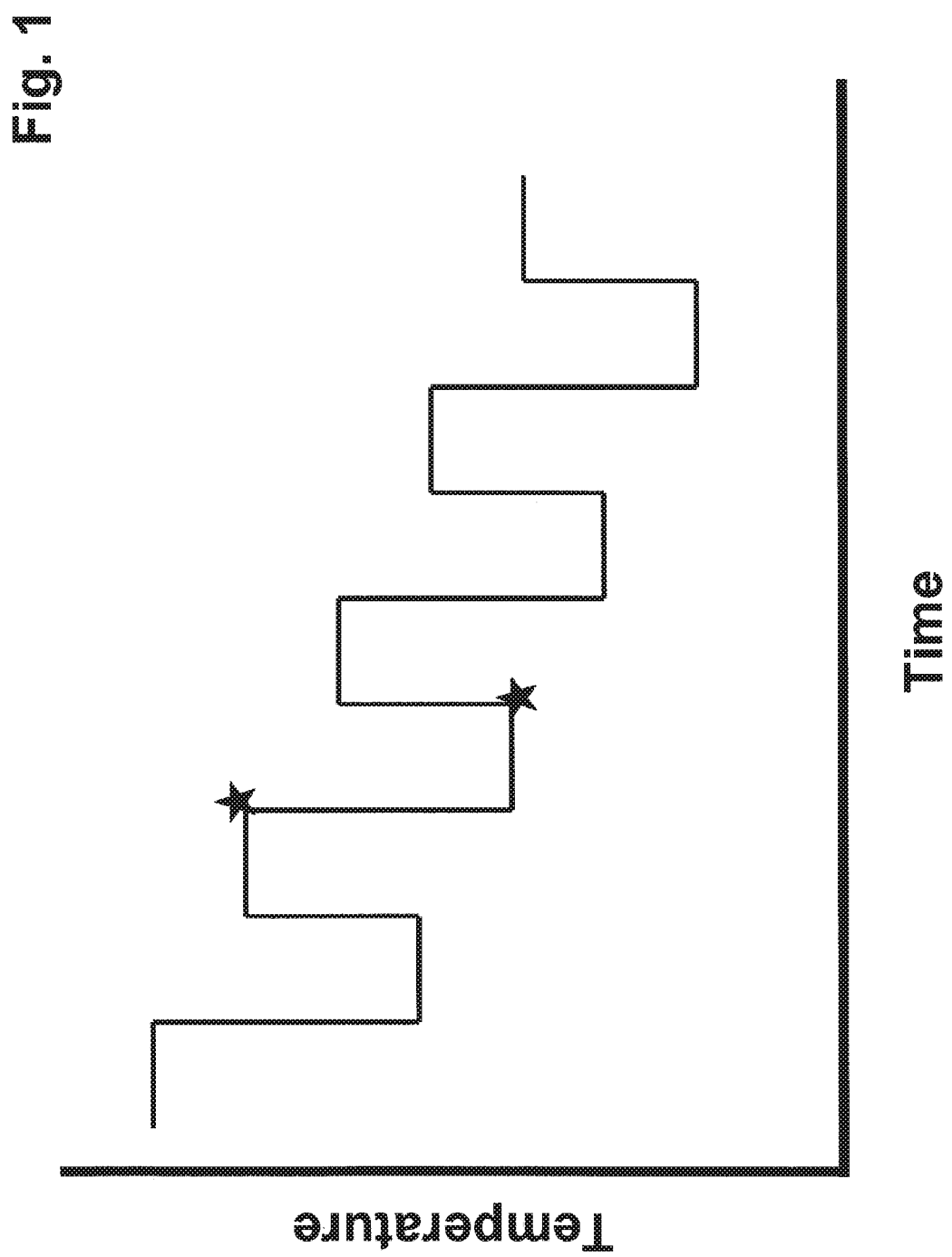
FIG. 1 is a graph showing one example of a square wave temperature profile. Temperature is shown in the Y-axis and time is shown in the X-axis. Stars indicate the times during the profile where detection of a signal is performed.

Provided herein are methods and systems to resolve nucleic acid structures based on the dissociation temperature between single and double-stranded forms, also known as a melting curve. The methods and systems make use of a square wave thermal profile with steps and involve the measurement of fluorescence at the high and low points at each step.

Traditional melting curve analysis involves frequent optical sampling of a solution volume that contains a reporting agent that changes its reporting property, e.g. intensity, as double-stranded DNA dissociates in response to an increase in temperature. However, high precision melt methods are limited in their ability to accurately and reproducibly report a melting temperature due to several issues. For example, in standard melt curve analysis, it is difficult to obtain uniformity of thermal control, and accuracy from solution to solution is difficult to reproduce. In addition, melting is not a crisp phenomenon, and the transition between double-stranded and single-stranded forms has some breadth because the transition includes a mix of thermodynamic and kinetic aspects. Also, traditional melt methods usually depend on the derivative of the fluorescence v. temperature trace to deconvolve overlapping melt signatures. However, the resolution of derivative peaks is often limited by noise in the fluorescence reads.

In order to achieve good resolution of nucleic acid structures that have similar melt temperatures, traditional melting curves are usually collected with very slow and precise control of the thermal cycling unit. The thermal profile used in traditional analysis is linear with extremely shallow slopes, compared to the slopes used in an amplification reaction. However, in many cases, the slope is difficult to control precisely and this manifests in variation of the melt temperature result due to uncertainty of the applied temperature. As a result, the time to measure is long to allow for slow transition in temperature and optical measurements which are taken frequently in the temperature domain to overcome noise limits of the optical system.

Furthermore, the optical scanners for some devices are not well suited to traditional melting curve analysis because the frequency of readings required is often greater than the capacity of the scanner to read all samples. As such, alternatives with traditional scanning devices include either: 1) slowing down the thermal ramp rate to accommodate the optical scan head (however, this increases run time and puts more limitations on the thermal control system); or 2) performing melting curves on one sample at a time (also increasing the overall length of run time).

In view of the above limitations of traditional melting curve analysis, it has been surprisingly discovered that melting curve analysis can be performed in a format analogous to scanning voltammetry. Specifically, the problems encountered in resolving electrochemistry of mixed solutions using scanning voltammetry is analogous in certain aspects to the problems encountered in traditional melting curve analysis. The analogy for the thermal profile is the scan of voltage applied to an electrode. A resolution of mixtures in electrochemistry is to use square wave profiles superimposed on a linear ramp.

Accordingly, presented herein is the surprising discovery of a new format for melting curve analysis that allows rapid determination of the melting temperature of a duplex nucleic acid molecule or mixture of different duplex nucleic acid molecules. In certain embodiments, the method comprises: subjecting a solution comprising a double-stranded nucleic acid molecule to a square wave temperature gradient, the gradient comprising a range of temperatures that causes at least one transition of the double-stranded nucleic acid molecule to single-stranded nucleic acid molecules; and detecting the at least one transition over the course of the square wave temperature gradient.

As used herein, the term square wave refers to an oscillating pattern generally defined by a staircase-like profile. In the context of thermal profiles, a square wave pattern alternates between high temperatures and low temperatures with instantaneous or near-instantaneous transitions. However, an ideal square wave is typically not achieved in practice because of physical limitations of the system that generates the waveform. The times taken for the signal to rise from the low level to the high level and back again are often referred to as the rise time and the fall time, respectively. Depending on the thermal cycling system in use, the rise time and fall time will vary from near-instantaneous to some finite time. As such, it will be appreciated that the transitions between high and low levels, and between low levels and high levels, may not result in a thermal profile that has vertical transitions. Thus, the term square wave can includes patterns where the slope of temperature transitions has some positive or negative slope when plotted as a function of temperature over time.

Additionally, the square wave profiles presented herein can include a hold time at each of the high and low temperatures. The length of the hold time can vary as needed to allow for detection of transitions between double-stranded and single-stranded nucleic acid. Thus, in embodiments where detection is instantaneous, hold time can be zero or near zero. In other embodiments, detection may involve some finite time and therefore the high or low temperature can be maintained as long as needed to detect whether nucleic acids are in single-stranded or double-stranded form. In some embodiments, the hold time can be adjusted as needed to allow the nucleic acid molecules to reach equilibrium. In some embodiments, hold time can be about 0 seconds, less than about 1 nanosecond, less than about 10 nanoseconds, less than about 100 nanoseconds, less than about 1 microsecond, less than about 10 microseconds, less than about 100 microseconds, less than about 1 millisecond, less than about 10 milliseconds, less than about 100 milliseconds, less than about 1 second, less than about 2, 3, 4, 5, 6, 7, 8, 9, or 10 seconds, or 10 seconds or more.

The square wave temperature profiles presented herein typically are superimposed on a temperature gradient. As used herein, a temperature gradient refers to a change in temperature over time. In traditional melt curve analysis, temperature gradients are linear and have a shallow slope in order to tightly control temperature. In the temperature profiles presented herein, temperature gradients can either have an overall positive or overall negative slope. Thus, when a square wave pattern is superimposed upon a positive slope temperature gradient or a negative slope temperature gradient, the resulting pattern resembles an ascending or descending staircase, as shown in FIGS. 1 and 2.

Accordingly, in certain embodiments, the square wave temperature gradient comprises a series of temperature pulses, each pulse comprising: increasing the temperature of the solution to a first high temperature; decreasing the temperature of the solution to a second low temperature; wherein the first high temperature is greater than the second low temperature. In embodiments where the temperature profile has an overall positive slope, in subsequent pulses, the first high temperature and the second low temperature are typically each adjusted to be greater than the first and second temperatures, respectively, in prior pulses. In embodiments where the temperature profile has an overall negative slope, in subsequent pulses, the first high temperature and the second low temperature are typically each adjusted to be lower than the first and second temperatures, respectively, in prior pulses. It will be appreciated that in some embodiments, high and low temperatures can remain the same between one or more pulses and still result in a temperature profile with an overall positive or negative slope. Similarly, in some embodiments, high and low temperatures in one more pulses can be lower than prior pulses and still result in a temperature profile with an overall positive slope. Likewise, in some embodiments, high and low temperatures in one more pulses can be higher than prior pulses and still result in a temperature profile with an overall negative slope.

In certain embodiments, at least one of the temperature pulses can comprise a range of temperatures wherein a detectable transition occurs between double-stranded nucleic acid molecules and single-stranded nucleic acid molecules. For example, a profile with a positive overall slope typically begins with pulses that comprise a high and a low temperature that each are below the melting point of a duplex nucleic acid. Likewise, a profile with a negative overall slope typically begins with pulses that comprise a high and a low temperature that each are above the melting point of a duplex nucleic acid. In such embodiments, one or more subsequent pulses pass through the melting temperature of the duplex nucleic acid and the transition of double-stranded to single-stranded nucleic acid, or the transition of single-stranded to double-stranded nucleic acid is detected.

As used herein, a detectable transition refers to a change in a signal that is indicative of the presence or absence of duplex nucleic acid. In order to identify detectable transitions, the present methods employ detection of the signal at one or more points in the temperature pulses. In certain embodiments, detection occurs during each of the temperature pulses. It will be appreciated that in alternative embodiments, detection need not occur in each temperature pulse. For example, in detection systems where a single detector is not configured for simultaneous detection of multiple samples, the detector could detect the signal during a first pulse for a first sample, and then detect a signal during a second pulse for a second sample.

In order to identify one or more detectable transitions, detection takes place a multiple points during the temperature profile. In certain embodiments, detection is timed to take place at discrete points in a pulse. For example, in some embodiments, detecting occurs at the high temperature and the low temperature in each of the temperature pulses. In some embodiments, detecting can take place throughout the temperature profile, and is continuous or near-continuous.

The methods and systems provided herein can further comprise identification of a temperature pulse having a maximum detectable transition from double-stranded nucleic acid to single-stranded nucleic acid molecules. By way of analogy to traditional melting curves, the melting temperature is typically identified by taking a derivative of the signal vs. temperature curve. The derivative serves to identify one or more inflection points that are indicative of the melting temperature of a particular nucleic acid species in the sample. The melting temperature of a nucleic acid species is commonly referred to as the temperature of dissociation, where 50% of the species is in duplex form and 50% is in single-stranded form. The energy required to break the base-base hydrogen bonding between two strands of nucleic acid, and hence the melting temperature, is dependent on their length, GC content and their complementarity. Other factors which can affect the melting temperature include the salt concentration of a solution (See, for example, Sambrook et al., Molecular Cloning: A Laboratory Manual 2d Ed. (Cold Spring Harbor Laboratory, (1989); incorporated herein by reference), the pH of the solution, and the presence of detergents, counter ions, solvents and other factors known to those of skill in the art. In the methods presented herein, identification of a temperature pulse having a maximum detectable transition serves to pinpoint the melting temperature without having to perform the additional derivative analysis that is typically required for traditional melting curves. Thus, in certain embodiments, identifying the maximum detectable transition comprises calculating the difference in a detectable signal measured at the high temperature and at the low temperature within a single temperature pulse. The differences in detectable signal for each of the pulses are then compared to identify the pulse with the largest difference in signal between the high temperature and the low temperature.

The nucleic acid molecules in a particular solution can be entirely homogeneous, where each double-stranded nucleic acid species has the same primary sequence and complementary sequence and therefore the same melting temperature. In other embodiments, the solution can be heterogeneous, comprising a plurality of nucleic acid species, where two or more double-stranded species in the solution each have a different primary sequence and complementary sequence, compared to the primary sequence and complementary sequence of other double-stranded species. Thus, even nucleic acid species with only 1, 2, 3, 4, 5, 6, 7, 8, 9, 10, 11, 12, 13, 14, 15, 16, 17, 18, 19, or only 20 or more base pair differences can be distinguished based upon the unique melting temperature of each species.

The nucleic acid species in the methods and systems presented herein can be any nucleic acid species that has a detectable melting temperature. The term nucleic acid or oligonucleotide or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10): 1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114: 1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positively-charged backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp. 69-176). Several nucleic acid analogs are described in Rawls, C & E News Jun. 2, 1997 p. 35. All of these references are hereby expressly incorporated by reference. Modifications of the ribose-phosphate backbone may be done to facilitate the addition of labels, or to increase the stability and half-life of such molecules in physiological environments, for example. The term nucleoside includes nucleotides as well as nucleoside and nucleotide analogs, and modified nucleosides such as amino modified nucleosides. In addition, nucleoside includes non-naturally occurring analog structures. Thus for example the individual units of a peptide nucleic acid, each containing a base, are referred to herein as a nucleoside.

Accordingly, the nucleic acid species can be any form or analog of DNA, RNA, as well as artificial and synthetic variants thereof. The nucleic acid species can comprise any combination of naturally-occurring and non-natural nucleotide analogs. The nucleic acid species can comprise one or more nucleotides where the pentose sugar or the nucleotide base or one or more of the phosphate esters of the nucleotide has been replaced with its respective analog. In certain embodiments, exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., and may include associated counter ions. It will be appreciated that the above-listed, or any other modification to the nucleic acid species may affect the Tm of the species compared to its unmodified counterpart.

Nucleic acid molecules can comprise, but are not limited to, genomic DNA, cDNA, hnRNA, mRNA, rRNA, tRNA, small RNA molecules, including without limitation, miRNA and miRNA precursors, siRNA, stRNA, snoRNA, other non-coding RNAs (ncRNA), fragmented nucleic acid, nucleic acid obtained from the nucleus, the cytoplasm, subcellular organelles such as mitochondria or chloroplasts, and nucleic acid obtained from microorganisms or DNA or RNA viruses that may be present on or in a biological sample. The nucleic acid molecules can be, for example, linear, circular, hairpin or any other configuration which allows at least a portion of the nucleic acid molecule to form double-stranded interactions with another molecule, or with itself.

The nucleic acid molecules can comprise one or more universal bases. The term universal base is intended to refer to nucleotide analogs that form fewer hydrogen bonds with naturally occurring nucleotides, i.e., adenosine, guanine, thymine, and cytosine, than between naturally occurring nucleotides. Universal bases can be hydrophobic base analogs that lack hydrogen bonding groups, yet which can pack efficiently in duplex DNA can show little selectivity in pairing with natural bases. Millican, T. A., et al. (1984) *Nuc. Acids Res.* 12:7435-7453; Schweitzer, B. A., et al. (1995) *J. Am. Chem. Soc.* 117:1863-1872; Matray, T. J., et al. (1999) *Nature* 399: 704-708; Ogawa, A. K., et al. (2000) *J. Am. Chem. Soc.* 122:3274-3287, the disclosures of which are hereby expressly incorporated by reference in their entireties. Nucleobase analogs that can hybridize non-selectively to each of the native bases have been described. Van Aerschot, A., et al. (1995) *Nucl. Acids Res.* 23: 4363-4370; Zhang, P. et al. (1998) *Nucl. Acids Res.* 26: 2208-2215; Seela, F. et al. (1999), *Nucleosides Nucletodies* 18:425-441; Bergstrom, D. E., et al. (1997) *Nucl. Acids Res.* 25: 1935-1942; Asomova, O., et al. (1997) *Nucl. Acids Res.* 25: 1930-1934; Bergstrom, D. E., et al., (1995) *J. Am. Chem. Soc.* 117: 1201-1209; Loakes, D. et al. (1995) *Nucl. Acids Res.* 23: 2361-2366; Loakes, D. et al. (1995) *Nucl. Acids Res.* 22: 4039-4043; Nichols, R., et al., (1994) *Nature* 369: 492-493. As will be appreciated by those in the art, all known nucleic acid analogs may find use in the present invention. Non-limiting examples of universal bases useful in the methods and compositions described herein include:

deoxyinosine, dexoyribionucleotides of 3-nitropyrrole (1,2), or 4-,5-, or 6-nitro-indole, 1-(2'-deoxy-β-D ribofuranosyl)-4-nitropyrazole, and 1-(2'-deoxy-β-D ribofuranosyl)-4-nitroimidazole.

In some embodiments, the nucleic acids are peptide nucleic acids (PNA) which includes peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature ($T_m$) for mismatched versus perfectly matched basepairs. DNA and RNA typically exhibit a 2-4° C. drop in $T_m$ for an internal mismatch. With the non-ionic PNA backbone, the drop is closer to 7-9° C., therefore allowing for better detection of mismatches. Similarly, due to their non-ionic nature, hybridization of the bases attached to these backbones is relatively insensitive to salt concentration.

Deoxyinosine ("dI") is a preferred example of a universal base. Inosine is capable of forming two hydrogen bonds with either A, C, T, or G (See, Barker, R., Organic Chemistry of Biological Molecules, Prentice-Hall, N.J. (1971); See also, Martin et al. (1985), Nucl. Acids Res. 13(24): 8927-8938). Other preferred examples of universal bases include 1-(2'-deoxy-β-D ribofuranosyl)-3-nitropyrrole, 1-(2'-deoxy-β-D ribofuranosyl)-4-nitropyrazole, 1-(2'-deoxy-β-D ribofuranosyl)-4-nitroimidazole, and 1-(2'-deoxy-β-D ribofuranosyl)-4-nitroindole.

The terms double-stranded nucleic acid molecule, duplex nucleic acid, and like terms refer to a pair of nucleic acid molecules, or portions of the same molecule, that exist in a hydrogen-bonded, helical array typically associated with DNA. The terms double-stranded nucleic acid molecule, duplex nucleic acid, and like terms also refer to those paired molecules that are essentially double-stranded, meaning those that contain short regions of mismatch, such as a mono-, di- or tri-nucleotide, resulting from design or error either in chemical synthesis of the oligonucleotide priming site on the first nucleic acid strand or in enzymatic synthesis of the second nucleic acid strand. A double-stranded nucleic acid molecule may exist as double-stranded DNA or RNA, an RNA/DNA heteroduplex or an RNA/DNA copolymer, wherein the term "copolymer" refers to a single nucleic acid strand that comprises both ribonucleotides and deoxyribonucleotides. In typical embodiments, double-stranded nucleic acids are those which are capable of detection using any of a number of methodologies known to those of skill in the art for detecting double-stranded nucleic acid molecules, such as detection of fluorescence from intercalating dyes. The term single-stranded nucleic acid molecule, refers to a nucleic acid molecule or a portion thereof which does not exist in double-stranded form.

The double-stranded nucleic acid species will typically comprise two strands that are complementary or substantially complementary in one or more regions. As used herein, the terms complementary and substantially complementary refer to the hybridization or base pairing between nucleotides or nucleic acids, such as, for instance, between the two strands of a double-stranded DNA molecule or between an oligonucleotide primer and a primer binding site on a single stranded nucleic acid to be sequenced or amplified. Accordingly, substantially complementary sequences can refer to sequences ranging in percent identity from 100, 99, 98, 97, 96, 95, 94, 93, 92, 91, 90, 89, 85, 80, 75 or less, or any number in between, compared to the reference sequence.

Complementary nucleotides are, generally, A and T (or A and U), or C and G. Two single-stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more typically from about 98 to 100%.

Advantages

The present technology provides multiple surprising advantages over traditional melting curve analysis. First, square wave thermal cycling uses the design intent of a thermal cycling unit, namely the ability to change temperature rapidly, instead of trying to control the thermal cycling unit in a manner that goes against the design intent. The scan is done quickly using rapid thermal ramps instead of slow thermal gradients.

Second, the square wave method is inherently a derivative method so that no additional data treatment is necessary to determine the melting temperature. The waveform allows greater resolution of overlapping transitions, presuming that an optimized waveform is identified, with a small number of total measurements.

Third, a step function thermal profile is more sensitive because the reporter has the opportunity to flip between states (i.e. melted vs. annealed) many times during the course of a scan.

Fourth, the method is a subtractive technique so that background levels cause significantly less interference with the analytical signal.

The square wave thermal profile provides kinetic information because the reporter is flipped between states repeatedly. If the kinetics are limiting for one direction, then the shape of the response will be shifted.

The methods presented herein have the additional advantage of being readily performed on any thermal cycler unit with proper programming.

It will be appreciated that the square wave can be stepped from low to high temperature or vice versa. The pulse height of each square wave pulse can be adjusted to cover different temperature spans. Some typical embodiments can use a square wave height that is equal to half the breadth of the transition measured using traditional melting curves. The number of pulses measured at a given average temperature can be varied to decrease noise and increase precision, at the expense of overall measurement time.

The methods presented herein have some analogy to square wave voltammetry which is applied to electrochemical systems. In electrochemistry, the voltage is stepped in place of temperature.

FIG. 1 sets forth one embodiment of the square wave thermal profile. As shown in FIG. 1, a square wave staircase profile includes a square wave superimposed on a linear ramp. The overall ramp is a downward gradient of temperature with respect to time. The profile comprises multiple pulses during the course of the ramp. At each pulse, the solution is subjected to a broad temperature range, and a signal is detected at two points.

FIG. 2 represents another thermal profile ramp with overall increasing temperature over time. As indicated in FIG. 2, the temperature profile passes through a series of pulses. Each pulse includes a transition jump. As used herein, a transition jump is an increase in temperature to a high temperature ($T_H$), from a low temperature ($T_L$). In the embodiment shown in FIG. 2, with each subsequent pulse, $T_L$ is increased so that the $T_L$ in each subsequent pulse is greater than the $T_L$ in the prior pulse. Similarly, $T_H$ is increased so that the $T_H$ in each subsequent pulse is greater than the $T_H$ in the prior pulse. Within each pulse, the average temperature $T_i$ is defined as half of the sum of $T_L$ and $T_H$.

In some embodiments, duplex nucleic acid is detected via a reporter moiety having a signature detectable signal in the presence of duplex nucleic acid. In the thermal profile exemplified in FIG. 2, duplex nucleic acid is detected via a reporter moiety having a fluorescent signal in the presence of duplex nucleic acid. Fluorescence readings are taken at $T_L$ and $T_H$ within each pulse, yielding a low temperature reading ($FL_L$) and a high temperature reading ($FL_H$) for each pulse. The change in fluorescence ($\Delta FL$) for each pulse is the difference between $FL_H$ and $FL_H$ for that pulse.

Temperature Steps Between Pulses

As used herein, the temperature step for low temperatures in each pulse ($\Delta T_{stepL}$) can be described as the difference between the $T_L$ in one pulse and the $T_L$ in the prior pulse. Similarly, the temperature step for high temperatures in each pulse ($\Delta T_{stepH}$) can be described as the difference between the $T_H$ in one pulse and the $T_H$ in the prior pulse. It will be appreciated that $\Delta T_{stepL}$ or $\Delta T_{stepH}$ can be any change in temperature that results in an overall positive slope or an overall negative slope in temperature over time. Thus, a series of pulses with a positive $\Delta T_{stepL}$ and/or $\Delta T_{stepH}$ would generate an overall positive slope. Likewise, a series of pulses with a negative $\Delta T_{stepL}$ and/or $\Delta T_{stepH}$ would generate an overall negative slope.

As used herein, a positive overall slope refers to a profile where the average $\Delta T_{stepL}$ and/or $\Delta T_{stepH}$ is positive. Typically, a profile with a positive overall slope begins with $T_L$ and $T_H$ temperatures that are below the melting point of duplex DNA. Typically, a profile with a positive overall slope ends with $T_L$ and $T_H$ temperatures that are above the melting point of duplex DNA.

Accordingly, in some embodiments, the overall slope is positive. In some such embodiments, each $\Delta T_{step}$ will be positive for the entire profile. For example, in typical embodiments, each subsequent $T_L$ will be greater than each of the preceding $T_L$ values. It will be appreciated, however, that in certain embodiments where the thermal profile has a positive slope, one or more $T_L$ values can be lower than a preceding $T_L$ value and still result in a profile with a positive overall temperature slope over time. Similarly, in some embodiments with a positive overall slope, each subsequent $T_H$ value will be greater than each of the preceding $T_H$ values. It will be appreciated, however, that in certain embodiments where the thermal profile has a positive slope, one or more $T_H$ values can be lower than a preceding $T_H$ value and still result in a profile with a positive overall temperature slope over time.

As used herein, a negative overall slope refers to a profile where the average $\Delta T_{stepL}$ and/or $\Delta T_{stepH}$ is negative. Typically, a profile with a negative overall slope begins with $T_L$ and $T_H$ temperatures that are above the melting point of duplex DNA. Typically, a profile with a negative overall slope ends with $T_L$ and $T_H$ temperatures that are below the melting point of duplex DNA.

Accordingly, in certain embodiments, the overall slope is negative. In some such embodiments, each $\Delta T_{step}$ will be negative for the entire profile. For example, in typical embodiment, each subsequent $T_L$ will be lower than each of the preceding $T_L$ values. It will be appreciated, however, that in certain embodiments where the thermal profile has a negative slope, one or more $T_L$ values can be greater than a preceding $T_L$ value and still result in a profile with a negative overall temperature slope over time. Similarly, in a typical thermal profile with a negative overall slope, each subsequent $T_H$ value will be lower than each of the preceding $T_H$ values. It will be appreciated, however, that in certain embodiments where the thermal profile has a negative slope, one or more $T_H$ values can be greater than a preceding $T_H$ value and still result in a profile with a positive overall temperature slope over time.

Accordingly, in some embodiments, the absolute value of $\Delta T_{stepL}$ can be, for example, less than about 0.001° C., or about 0.001° C., 0.01° C., 0.1° C., 0.2° C., 0.3° C., 0.4° C., 0.5° C., 0.6° C., 0.7° C., 0.8° C., 0.9° C., 1.0° C., 1.1° C., 1.2° C., 1.3° C., 1.4° C., 1.5° C., 1.6° C., 1.7° C., 1.8° C., 1.9° C., 2.0° C., 2.1° C., 2.2° C., 2.3° C., 2.4° C., 2.5° C., 2.6° C., 2.7° C., 2.8° C., 2.9° C., 3.0° C., 3.1° C., 3.2° C., 3.3° C., 3.4° C., 3.5° C., 3.6° C., 3.7° C., 3.8° C., 3.9° C., 4.0° C., 4.1° C., 4.2° C., 4.3° C., 4.4° C., 4.5° C., 4.6° C., 4.7° C., 4.8° C., 4.9° C., 5.0° C., 5.1° C., 5.2° C., 5.3° C., 5.4° C., 5.5° C., 5.6° C., 5.7° C., 5.8° C., 5.9° C., 6° C., 7° C., 8° C., 9° C., 10° C., 11° C., 12° C., 13° C., 14° C., 15° C., 16° C., 17° C., 18° C., 19° C., about 20° C., or more, as well as any temperature value therebetween. In typical embodiments, the absolute value of $\Delta T_{stepL}$ ranges from between about 1.0° C. to about 5.0° C. In some embodiments, the $\Delta T_{stepL}$ is the same for each pulse in the profile. For example, as shown in FIG. 2, the $\Delta T_{stepL}$ is the same for each pulse. It will be appreciated that in other embodiments, the $\Delta T_{stepL}$ can be different among one or more pulses in the profile.

Similarly, in some embodiments, the absolute value of $\Delta T_{stepH}$ can be, for example, less than about 0.001° C., or about 0.001° C., 0.01° C., 0.1° C., 0.2° C., 0.3° C., 0.4° C., 0.5° C., 0.6° C., 0.7° C., 0.8° C., 0.9° C., 1.0° C., 1.1° C., 1.2° C., 1.3° C., 1.4° C., 1.5° C., 1.6° C., 1.7° C., 1.8° C., 1.9° C., 2.0° C., 2.1° C., 2.2° C., 2.3° C., 2.4° C., 2.5° C., 2.6° C., 2.7° C., 2.8° C., 2.9° C., 3.0° C., 3.1° C., 3.2° C., 3.3° C., 3.4° C., 3.5° C., 3.6° C., 3.7° C., 3.8° C., 3.9° C., 4.0° C., 4.1° C., 4.2° C., 4.3° C., 4.4° C., 4.5° C., 4.6° C., 4.7° C., 4.8° C., 4.9° C., 5.0° C., 5.1° C., 5.2° C., 5.3° C., 5.4° C., 5.5° C., 5.6° C., 5.7° C., 5.8° C., 5.9° C., 6° C., 7° C., 8° C., 9° C., 10° C., 11° C., 12° C., 13° C., 14° C., 15° C., 16° C., 17° C., 18° C., 19° C., about 20° C., or more, as well as any temperature value therebetween. In typical embodiments, the absolute value of $\Delta T_{stepH}$ ranges from between about 1.0° C. to about 5.0° C. In some embodiments, the $\Delta T_{stepH}$ is the same for each pulse in the profile. For example, as shown in FIG. 2, the $\Delta T_{stepH}$ is the same for each pulse. It will be appreciated that in other embodiments, the $\Delta T_{stepH}$ can be different among one or more pulses in the profile.

Temperature Transitions within Pulses

As used herein, the temperature transition jump height ($\Delta T_{trans}$) refers to the difference between the high temperature $T_H$ and the low temperature $T_L$ within a pulse. It will be appreciated that $\Delta T_{trans}$ can be any suitable temperature range. For example, in some embodiments, the $\Delta T_{trans}$ of a pulse can be, for example, less than about 0.001° C., or about 0.001° C., 0.01° C., 0.1° C., 0.2° C., 0.3° C., 0.4° C., 0.5° C., 0.6° C., 0.7° C., 0.8° C., 0.9° C., 1.0° C., 1.1° C., 1.2° C., 1.3° C., 1.4° C., 1.5° C., 1.6° C., 1.7° C., 1.8° C., 1.9° C., 2.0° C., 2.1° C., 2.2° C., 2.3° C., 2.4° C., 2.5° C., 2.6° C., 2.7° C., 2.8° C., 2.9° C., 3.0° C., 3.1° C., 3.2° C., 3.3° C., 3.4° C., 3.5° C., 3.6° C., 3.7° C., 3.8° C., 3.9° C., 4.0° C., 4.1° C., 4.2° C., 4.3° C., 4.4° C., 4.5° C., 4.6° C., 4.7° C., 4.8° C., 4.9° C., 5.0° C., 5.1° C., 5.2° C., 5.3° C., 5.4° C., 5.5° C., 5.6° C., 5.7° C., 5.8° C., 5.9° C., 6° C., 7° C., 8° C., 9° C., 10° C., 11° C., 12° C., 13° C., 14° C., 15° C., 16° C., 17° C., 18° C., 19° C., about 20° C., or more, as well as any temperature value therebetween. In typical embodiments, the $\Delta T_{trans}$ ranges from between about 5° C. to about 10° C. In some embodiments, the $\Delta T_{trans}$ is the same for each pulse in the profile. For example, as shown in FIG. 2, the $\Delta T_{trans}$ is the same for each pulse. It will be appreciated that in other embodiments, the $\Delta T_{trans}$ can be different among one or more pulses in the profile.

Although the $\Delta T_{trans}$ can be any suitable temperature range, one way to determine a useful $\Delta T_{trans}$ for a square wave thermal profile is to measure the temperature range corresponding to half of the pulse width in a traditional melting curve. Specifically, as shown in FIG. 3, a traditional melting curve measure the fluorescence of an intercalating dye over temperature range from low to high. The traditional melting curve typically can be segmented into three temperature ranges: 1) a region of lower temperatures where fluorescence is relatively high and constant; 2) a transitional region where fluorescence levels drop as temperatures rise; and 3) a region of higher temperature where fluorescence is relatively low and constant. The melting temperature generally falls at the point in which the drop in fluorescence reaches an inflection point. Thus, for example, a transitional region in a traditional melting curve might span the 20° C. region ranging from 50° C. to 70° C. In such an example, one half of the transitional width would be a 10° C. span. Thus, were the same duplex nucleic acid to be analyzed using the thermal profiles presented herein, a useful transition jump height $\Delta T_{trans}$ would be 10° C., or one half of the transitional width in the traditional melting curve.

Systems and Devices

Also provided herein are systems for determining the melting temperature of a duplex nucleic acid molecule. The systems can include a programmable thermal cycling apparatus; a detector; and a program for square wave thermal cycling, wherein the program comprises instructions for: subjecting a solution comprising a double-stranded nucleic acid molecule to a square wave temperature gradient, the gradient comprising a range of temperatures that causes at least one transition of the double-stranded nucleic acid molecule to a single-stranded nucleic acid molecules; and detecting the at least one transition over the course of the square wave temperature gradient.

The programmable thermal cycling apparatus can be any suitable such apparatus which allows access for a detector to detect the transition in one or more nucleic acid samples. Programmable thermal cycling devices are known to those of skill in the art. For example, devices used for polymerase chain reaction are capable of rapid cycling between temperatures.

The detector can be any suitable detector that is capable of detecting the transition between single-stranded and double-stranded nucleic acid. Detectors for detecting fluorescence of reporter moieties such as intercalating dyes are well known in the art. Likewise, detectors for detecting UV absorbance are well known in the art. In some embodiments, the system further comprises a light source. The light source can be used where absorbance or fluorescence is used as the signature detectable signal in the presence of duplex nucleic acid. Light sources for UV absorbance, as well as light sources to provide excitation light for fluorescence are well known in the art.

As used herein, the term program refers to instructions or commands to perform a task or process. The term program can be used interchangeably with the term module. In certain embodiments, a program can be a compilation of various instructions executed under the same set of commands. In other embodiments, a program can refer to a discrete batch or file.

The program, as well as signal data acquired by the detector, can be stored on any suitable storage capacity. As used herein, the terms storage, storage device, storage capacity, and the like can refer to any medium, device or means of storage of information. Storage can include, but is not limited to, a disk drive device such as a hard drive, floppy disk, optical or magneto-optical disk, memory such as RAM or ROM chips, and any other medium used to record or store data. In some embodiments, a storage capacity is connected to a processor which sends information to be recorded on the storage capacity after it is acquired. In specific embodiments, signal data is acquired by a system and is recorded on a storage capacity. In other embodiments, signal data is acquired by a system and information is first processed, and the processed information is recorded on a storage capacity.

Detection of Duplex Nucleic Acid

In the methods provided herein, transitions between single-stranded and double-stranded nucleic acid are monitored via detection of a signal indicative of the level of duplex nucleic acid. Detection of duplex nucleic acid levels can be performed by any suitable methodology as is known in the art. For example, duplex nucleic acid levels can be detected using a reporter moiety having a signature detectable signal in the presence of duplex nucleic acid. Reporter moieties having a signature detectable signal in the presence of duplex nucleic acid are well known to those of skill in the art, and can produce any detectable signal. Typically, the signal is an optical signal, such as fluorescent, colorimetric, luminescent or turbidic. In some embodiments, the signal can be electrical, such as a change in voltage, resistance or current change.

In typical embodiments, the reporter moiety is an intercalating dye. Intercalating dyes show differential fluorescence emission dependent on their association with double-stranded or single-stranded DNA. Specifically, they bind specifically to double-stranded DNA and when they are bound they fluoresce brightly. In the absence of double stranded DNA they have nothing to bind to and they only fluoresce at a low level. Examples of suitable commercially available fluorescent dyes include SYBR Green, LC Green, LC Green Plus, ResoLight, EvaGreen, Chromofy, SYTO 9, ethidium bromide, YO-PRO-1, Hoechst 33258, and Pico Green. It will be appreciated that any suitable intercalating dye can be used which exhibits a signature detectable signal in the presence of duplex nucleic acid.

In typical embodiments, the signature detectable signal is reversible. As such, the signature detectable signal can in effect be turned "on" and "off" repeatedly as the temperature profile repeatedly passes through the melting temperature of a duplex nucleic acid in multiple pulses. Thus, intercalating dyes are well suited as reporter moieties because they preferentially bind to duplex nucleic acid, and when rising temperature causes melting of the duplex, the signal is then diminished until the temperature once again reaches levels where annealing can take place. It will be appreciated that any suitable reporter moiety which produces a reversible signal can be utilized in the methods presented herein.

In some embodiments, detection does not involve a reporter moiety, but can involve monitoring an inherent property of double-stranded or single-stranded nucleic acid. The inherent property can be any suitable property of double-stranded or single-stranded nucleic acid that allows one to monitor transitions between single-stranded and double-stranded nucleic acid. In some embodiments, the inherent property is UV absorbency. For example, single-stranded DNA absorbs ultraviolet light at 260 nm more strongly than double-stranded DNA. Accordingly, changes in absorbency at 260 nm or any other suitable wavelength can be used as a tool to the levels of double-stranded nucleic acids compared to single-stranded nucleic acids.

Kinetic Information

Melting of duplex nucleic acid is a phenomenon that includes a mix of thermodynamic and kinetic aspects. In a traditional melt curve analysis, kinetic data, often seen as asymmetry in the melt curve, may be obscured by noise. Advantageously, the present methods can provide insights into the kinetics of the transition, because the nucleic acid molecules are flipped between states repeatedly. If there is a tendency for the transition to occur faster in one direction compared to the other, it can be identified as the profile passes repeatedly through the transition temperature.

Accordingly, presented herein is a method of determining kinetic information about a double-stranded to single-stranded transition for nucleic acids, the method comprising: providing a sample comprising double-stranded nucleic acid molecules and a reporter moiety having a signature detectable signal in the presence of duplex nucleic acid; subjecting the sample to a series of temperature pulses, wherein the pulses cause the double-stranded nucleic acid molecules to transition to single-stranded molecules and back to double-stranded molecules; and detecting, using the signal produced by the reporter moiety, the rate of transition between single-stranded and double-stranded states, whereby the rate of transition between the states provides kinetic information about the transition.

Having generally described this invention, a further understanding can be obtained by reference to certain specific examples which are provided herein for purposes of illustration only, and are not intended to be limiting.

EXAMPLES

Example 1—Use of Square Wave Thermal Profile to Detect Heterozygosity of a Polymorphism in a Patient Population The following prospective example illustrates one application of the square wave thermal profiles described hereinabove. To detect the presence of a polymorphism within a patient population, genomic DNA samples are collected from a panel of patients in the population. The region of interest is amplified by polymerase chain reaction, using primers that flank the potential polymorphism. Specifically, primers are designed which will amplify the region containing the polymorphism. As a result of the primer design amplification products are produced having distinct sequence in the region of the polymorphism, depending on which specific allele is amplified. Thus, the products will also have melting temperatures which differ by at least 1.5° C., depending on which allele is amplified.

The PCR products are each subjected to a melting curve analysis. SYBR Green is added to each sample, which is then placed in the thermal cycling/detection apparatus. The melting curve temperature profile begins at 45° C. and follows a square wave pattern, with 5° C. transitions and 2° C. steps for the low and high temperatures for each pulse. The profile follows this pattern of pulses until it reaches a final temperature of 76° C.

Analysis of the data identifies pulses maximal transitions in fluorescence values. In some of the samples, two $T_m$ points are identified at temperatures which differ by 1.5 to 2.0° C. In other samples, a single $T_m$ point only is identified at either of the two temperatures. Based on these findings, patient samples are sorted as either heterozygous for the polymorphism or homozygous positive or negative.

The above description discloses several methods and systems of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein including, but not limited to, published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

What is claimed is:

1. A system for determining the melting temperature of a duplex nucleic acid molecule, said system comprising:
   a programmable thermal cycling apparatus;
   a detector; and
   a program for square wave thermal cycling, said program comprising instructions for:
      subjecting a solution comprising a double-stranded nucleic acid molecule to a square wave temperature gradient, said gradient comprising a range of temperatures that causes at least one transition of said double-stranded nucleic acid molecule to a single-stranded nucleic acid molecules; and
      detecting said at least one transition over the course of said square wave temperature gradient,
      wherein said square wave temperature gradient comprises a series of temperature pulses, each pulse comprising:
         a) increasing the temperature of said solution to a first high temperature, and
         b) decreasing the temperature of said solution to a second low temperature, wherein said first high temperature is greater than said second low temperature, and
      wherein, in subsequent pulses, said first high temperature and said second low temperature are each adjusted to be greater than the first and second temperatures, respectively, in prior pulses.

2. The system of claim 1, wherein at least one of said temperature pulses comprises a range of temperatures wherein a detectable transition occurs between said double-stranded nucleic acid molecule and said single-stranded nucleic acid molecules.

3. The system of claim 1, wherein said detecting occurs at said first high temperature and said second low temperature in each of said temperature pulses.

4. The system of claim 1, wherein said program further comprises instructions for:
   identifying a temperature pulse having a maximum detectable transition from double-stranded nucleic acid to single-stranded nucleic acid molecules.

5. The system of claim 4, wherein said identifying comprises calculating the difference in a detectable signal, said detectable signal measured at said first high temperature and said second low temperature within a single temperature pulse.

6. The system of claim 1, wherein said instructions for detecting comprise instructions for monitoring ultraviolet (UV) absorbency.

7. The system of claim 1, wherein said instructions comprise instructions for generating the square wave temperature gradient.

8. The system of claim 1, wherein said instructions comprise instructions for subjecting the solution comprising the double-stranded nucleic acid molecule to a square wave temperature gradient comprising a range of temperatures that includes a melting temperature of the duplex nucleic acid molecule.

9. The system of claim 4, wherein identifying the temperature pulse having a maximum detectable transition comprises calculating a difference in a detectable signal, the detectable signal measured by the detector at the first high temperature and at the second low temperature within a single temperature pulse.

10. The system of claim 1, wherein the detector is configured to detect a reporter moiety having a signature detectable signal in the presence of duplex nucleic acid.

11. The system of claim 10, wherein the detector is configured to detect a reporter moiety having a signature detectable signal that is reversible.

12. The system of claim 10, wherein the detector is configured to detect a reporter moiety comprising a fluorescent dye.

13. The system of claim 10, wherein the detector is configured to detect a reporter moiety selected from the group consisting of: ethidium bromide, YO-PRO-1, Hoechst 33258, Pico Green, and SYBR Green.

14. The system of claim 1, further comprising a light source.

15. A system for determining the melting temperature of a duplex nucleic acid molecule, the system comprising:
a programmable thermal cycling apparatus;
a detector; and
a program for square wave thermal cycling, the program comprising instructions for:
subjecting a solution comprising single-stranded nucleic acid molecules to a square wave temperature gradient, the gradient comprising a range of temperatures that causes at least one transition of the single-stranded nucleic acid molecules to double-stranded nucleic acid molecules; and
detecting the at least one transition over the course of the square wave temperature gradient,
wherein the square wave temperature gradient comprises a series of temperature pulses, each pulse comprising:
a) increasing the temperature of the solution to a first high temperature, and
b) decreasing the temperature of the solution to a second low temperature, wherein the first high temperature is greater than the second low temperature, and
wherein, in subsequent pulses, the first high temperature and the second low temperature are each adjusted to be less than the first and second temperatures, respectively, in prior pulses.

16. The system of claim 15, wherein the instructions comprise instructions for subjecting the solution comprising the single-stranded nucleic acid molecules to a square wave temperature gradient comprising a range of temperatures that includes a melting temperature of the duplex nucleic acid molecule.

17. The system of claim 15, wherein at least one of the temperature pulses comprises a range of temperatures wherein a detectable transition occurs between the single-stranded nucleic acid molecules and the double-stranded nucleic acid molecules.

* * * * *